US009375553B2

(12) United States Patent
Chrisman

(10) Patent No.: US 9,375,553 B2
(45) Date of Patent: Jun. 28, 2016

(54) COMPRESSION TORQUE DEVICE

(71) Applicant: Freddy Dwight Chrisman, Little Rock, AR (US)

(72) Inventor: Freddy Dwight Chrisman, Little Rock, AR (US)

(*) Notice: Subject to any disclaimer, the term of this patent is extended or adjusted under 35 U.S.C. 154(b) by 85 days.

(21) Appl. No.: 14/262,240

(22) Filed: Apr. 25, 2014

(65) Prior Publication Data
US 2014/0324026 A1    Oct. 30, 2014

Related U.S. Application Data

(60) Provisional application No. 61/816,091, filed on Apr. 25, 2013.

(51) Int. Cl.
*A61B 5/00* (2006.01)
*A61M 25/09* (2006.01)

(52) U.S. Cl.
CPC ............ *A61M 25/09041* (2013.01); *A61M 2025/09116* (2013.01)

(58) Field of Classification Search
CPC .......... A61M 25/09; A61M 25/09041; A61M 25/0905; A61M 2025/09116; A61M 2025/09125
USPC ........................................................ 600/585
See application file for complete search history.

(56) References Cited

U.S. PATENT DOCUMENTS

| | | | | |
|---|---|---|---|---|
| 5,312,338 A * | 5/1994 | Nelson | ................... | A61B 17/22 600/434 |
| 5,325,868 A * | 7/1994 | Kimmelstiel | .......... | A61B 17/22 600/585 |
| 6,714,809 B2 * | 3/2004 | Lee | ........................ | A61B 5/055 439/578 |
| 7,455,660 B2 * | 11/2008 | Schweikert | ..... | A61M 25/09041 600/585 |
| 7,717,865 B2 * | 5/2010 | Boutillette | ...... | A61M 25/09041 600/585 |
| 8,700,130 B2 * | 4/2014 | Iddan | ................... | A61B 6/5217 600/424 |
| 8,840,568 B2 * | 9/2014 | Kimura | ........... | A61M 25/09041 206/364 |
| 8,926,529 B2 * | 1/2015 | Rollins | ........... | A61M 25/09041 600/528 |
| 9,011,351 B2 * | 4/2015 | Hoshinouchi | ... | A61M 25/09041 600/585 |
| 9,050,438 B2 * | 6/2015 | Rollins | ........... | A61M 25/09041 |

* cited by examiner

*Primary Examiner* — Max Hindenburg
(74) *Attorney, Agent, or Firm* — Dunlap, Bennett & Ludwig PLLC

(57) ABSTRACT

An interventional guidewire assembly with improved guidewire control includes a guidewire and a housing having a first opening that accommodates the guidewire and a second opening. The assembly further includes an actuator that passes through the second opening that is actuated by a finger in a direction substantially perpendicular to an axis of the guidewire. The assembly further includes a clamp operably coupled to the actuator that compresses the guidewire to couple the guidewire to the housing when pressure is applied to the actuator. The assembly further includes a return spring that supplies pressure to remove the clamp from the guidewire.

11 Claims, 3 Drawing Sheets

COMPRESSION TORQUE DEVICE

TECHNICAL FIELD

The apparatus described herein generally relates to the field of medical devices. More specifically, the apparatus relates to guidewires for interventional procedures.

BACKGROUND

Maintaining accurate control and placement of a guidewire during a medical interventional procedure is essential. Present torque devices used to accomplish this task require excessive manipulation with more than one hand or excessive force parallel to the guide wire axis in order to correctly position the device. This can divert the attention of the interventionalist during the procedure and increase the chance of unwanted movement of the wire in the patient, which could lead to complications.

The current devices require release of the secure hand position on the guidewire in order to adjust the positioning of the torque device. These moments of release of the guidewire could result in unexpected advancement or retraction of the guidewire that could lead to problems during the procedure As can be seen, there is a need for an improved torque devices for guidewires. This apparatus should permit blind one-handed operation and not require substantial force in a direction parallel to the guidewire axis to manipulate.

BRIEF SUMMARY

An interventional guidewire assembly with improved guidewire control includes a guidewire and a housing having a first opening that accommodates the guidewire and a second opening. The assembly further includes an actuator that passes through the second opening that is actuated by a finger in a direction substantially perpendicular to an axis of the guidewire. The assembly further includes a clamp operably coupled to the actuator that compresses the guidewire to couple the guidewire to the housing when pressure is applied to the actuator. The assembly further includes a return spring that supplies pressure to remove the clamp from the guidewire.

In some embodiments, the assembly includes a retention spring that supplies pressure to compress the clamp against the guidewire. In some embodiments, the return spring and the retention spring are two layers on a single leaf spring. In some embodiments, the clamp is a collet. In some embodiments, the assembly includes a sleeve that compresses the collet against the guidewire when the actuator is actuated. In some embodiments, the assembly includes a wire guide disposed in the housing in contact with the guidewire opposite the actuator, and the clamp comprises the wire guide and the actuator. In some embodiments, the assembly includes a ratchet that retains the clamp compressed against the guidewire after the actuator has been actuated. In some embodiments, the ratchet rotates relative to the housing. In some embodiments, the assembly further includes a pivot that couples the actuator to the housing and allows relative rotation between the actuator and the housing when pressure is applied to the actuator. In some embodiments, the assembly includes a linkage that transfers motion from the actuator to the clamp and retains the clamp compressed against the guidewire after the actuator has been actuated.

An apparatus for precise control of a wire in two axes includes a housing having a first opening that accommodates the wire and a second opening. The apparatus further includes an actuator that passes through the second opening that is actuated by a finger in a direction substantially perpendicular to an axis of the wire. The apparatus further includes a clamp operably coupled to the actuator that compresses the wire to couple the wire to the housing when pressure is applied to the actuator. The apparatus further includes a return spring that supplies pressure to uncouple the clamp from the wire.

In some embodiments, the apparatus includes a retention spring that supplies pressure to compress the clamp against the wire. In some embodiments, the return spring and the retention spring are two layers on a single leaf spring. In some embodiments, the clamp is a collet. In some embodiments, the apparatus further includes a sleeve that compresses the collet against the wire when the actuator is actuated. In some embodiments, the apparatus further includes a wire guide disposed in the housing in contact with the wire opposite the actuator. In some embodiments, the clamp comprises the wire guide and the actuator. In some embodiments, the apparatus further includes a ratchet that retains the clamp compressed against the wire after the actuator has been actuated. In some embodiments, the ratchet rotates relative to the housing. In some embodiments, the apparatus further includes a pivot that couples the actuator to the housing and allows relative rotation between the actuator and the housing when pressure is applied to the actuator. In some embodiments, the apparatus further includes a linkage that transfers motion from the actuator to the clamp and retains the clamp compressed against the wire after the actuator has been actuated.

DETAILED DESCRIPTION

In several embodiments, the apparatus described herein is a compression torque device with compression activation and release. The apparatus described herein allows for single action of the finger to immediately secure the torque device to the guidewire. A subsequent finger manipulation causes immediate release of the torque device from the guidewire for adjustment to the next position. When secured, the apparatus facilitates single-handed rotational manipulation of the guidewire allowing for precise placement of the guidewire tip. This will allow single hand repositioning and manipulation of the torque device on the guidewire to allow the interventionalist to maintain precise control of the wire, with a single hand, without diverting attention away from the procedure image or the patient.

The apparatus described herein enables the interventionalist to maintain single hand position without eye to hand visual cues to secure and release the torque device for positioning.

The apparatus described herein also enables the interventionalist to be able to continuously maintain secure control of the guidewire during all repositioning. The downward force required to secure and release the embodiments described herein is perpendicular to the guidewire and therefore decreases potential for unexpected advancement or retraction. In other words, the device can be operated using only one-handed blind operation.

Figure 1:
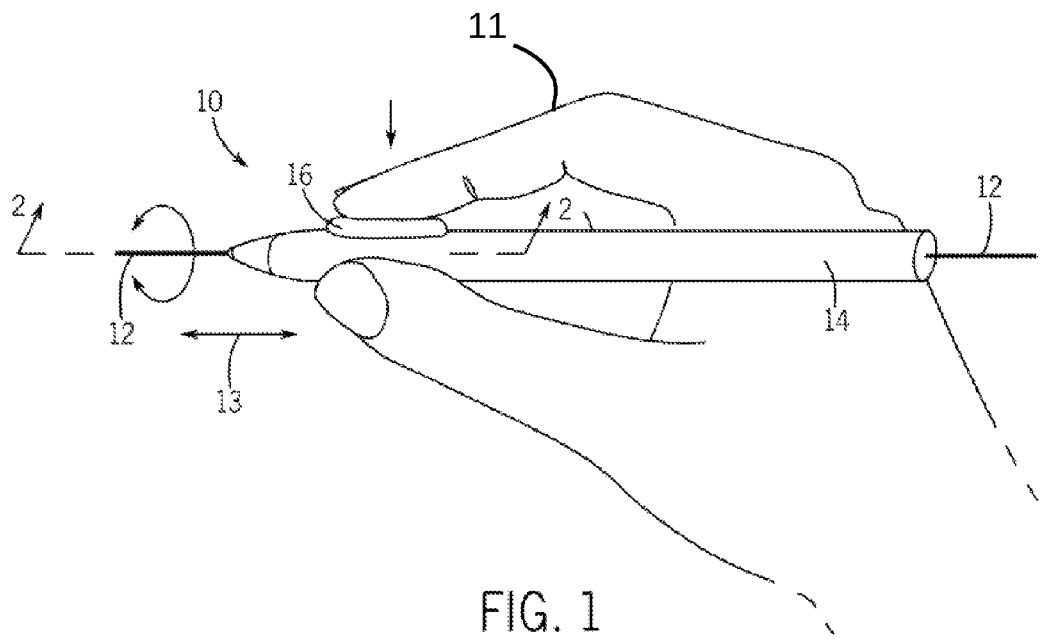
FIG. 1 is a perspective view of one embodiment of the apparatus in use.

FIG. 1 shows the apparatus in use during an operation. An operator compresses actuator 16 using finger 11. In this embodiment, finger 11 is an index finger. This action allows the user to toggle between a coupled mode where manipulation of apparatus 10 will translate into guidewire 12, and an uncoupled mode where apparatus 10 moves independently of guidewire 12. The user can move guidewire 12 in two axes (longitudinal and rotational) by applying corresponding force to housing 14 of apparatus 10. In coupled mode, the user can move the guidewire in an axial direction 13 or a rotation direction 12 using apparatus 10. In uncoupled mode, the user can move apparatus 10 in those directions while not moving guidewire 12.

Figure 2:
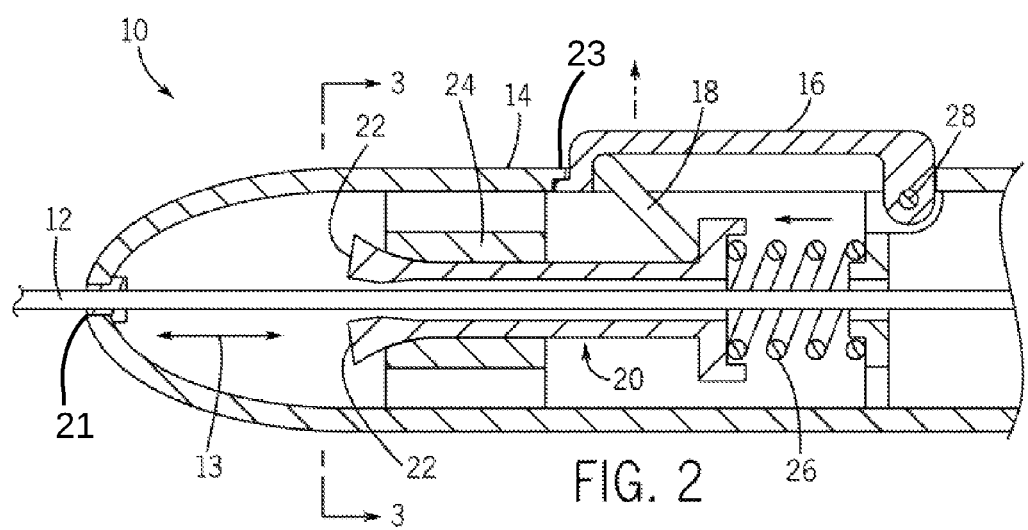
FIG. 2 is a detail longitudinal sectional view taken on line 2-2 of FIG. 1, showing the apparatus in an uncoupled configuration.
Figure 3:
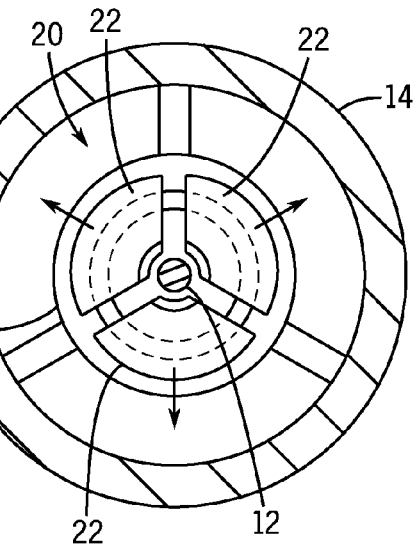
FIG. 3 is a cross-sectional view taken on line 3-3 of FIG. 2.

FIGS. 2 and 3 show the apparatus in an uncoupled configuration. In an uncoupled mode, the torque device 10 may travel either backwards or forwards 13 on wire 12, or rotate relative to wire 12. Apparatus 10 comprises a clamping mechanism, in this case a collet unit 20 (consisting of clamping fingers 22) and tapered sleeve 24. Actuator 16 transfers motion to collet unit 20 via linkage 18. Compression of actuator 16 thereby results in a movement of collet unit 20 in a proximal axial direction, resulting in the compression of collet fingers 22 by tapered sleeve 24 against guidewire 12. Clamping fingers 22 have a surface that comes in contact with and secures guidewire 12. Return spring 26 applies a force in the distal axial direction against collet unit 20, which separates collet fingers 22 from guidewire 12. Pivot 28 couples actuator 16 to housing 14 and permits a rotational movement between actuator 16 and housing 14. As a result, actuator 16 is compressed in a direction perpendicular to an axis 13 of guidewire 12, giving a user greater control over guidewire 12.

The end of the housing 14 may be various shapes to accept the wire 12, and comprise a first opening 21 to thread guidewire 12. In this embodiment, the actuator 16 is a button that fits within a second opening 23 in housing 14 with variable degrees of rise from the surface in order to provide a distance to compress in order to engage or disengage the compression mechanism 20. Actuator 16 may be located on one or more sides of the device 10 along its longitudinal body. In this embodiment, the housing 14 has a cylindrical shape in order to easily rotate or hold between the tips of fingers 11. The housing 14 may provide a slot 23 for the compression button 16 to extend through and enough space within the housing 14 for the compression mechanism 20 and a slot 21 to pass the wire 12 the length of the device 10.

Tapered sleeve 24 may be designed with variable slotted and angled edges that communicate with collet unit 20 to allow for the rotation of tapered sleeve 24 relative to collet unit 20 that enables the clamping fingers 22 to be engaged and/or disengaged at alternating depths/distances. The collet unit 20 may be designed with angles leading to variable communication points with the external slotted and angled edges of the tapered sleeve 24. The collet unit 20 may remain fixed in housing 14. The spring 26 may be of variable spring types and may apply perpendicular force to the passed wire 12 by connection to the slotted tapered sleeve 24 and the clamping fingers 22.

The cylindrical housing 14 may be shaped in order to be held by one hand between tips of fingers 11 in order to maintain precise longitudinal and rotational control. The housing 14 surface may have a variable texture to help maintain control. The center of the housing 14 may be slotted in order to pass a wire 12 of various diameters through the torque device 10. There may be one or more compression buttons 16 at various angles along the cylindrical housing 14 that may provide an external means to compress and hold a wire 12 passed through the torque device 10. The fixed and compressed position allows the pressed wire 12 to be maintained in a fixed position. Once the clamping fingers 22 and spring 26 are disengaged by pressing the compression button 16 again, the housing 14 may be freely moved in a longitudinal or rotational fashion along the wire 12. The apparatus described herein may allow for single hand manipulation of the torque device 10 along the wire 12 in order to reposition the device with minimal unintentional movement of the wire 12.

Figure 4:
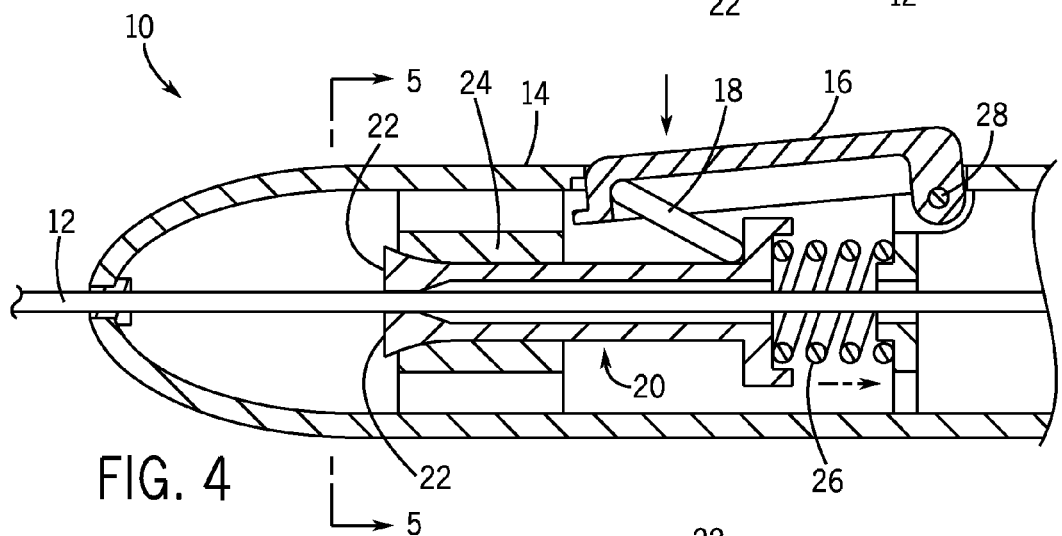
FIG. 4 is a detail longitudinal sectional view similar to FIG. 2, showing the embodiment of FIG. 1 in a coupled configuration.
Figure 5:
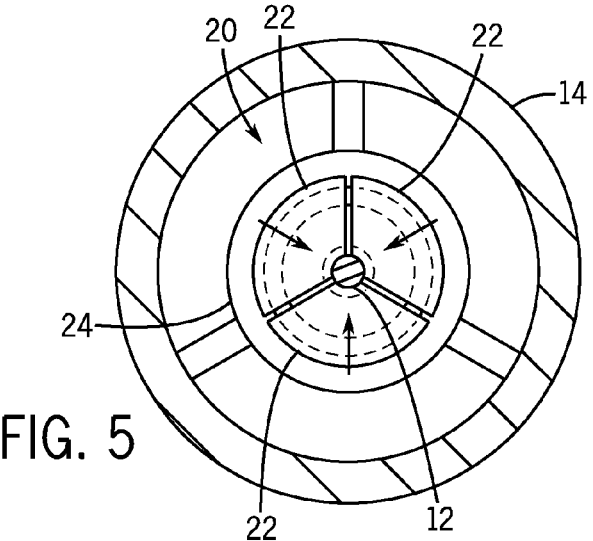
FIG. 5 is a cross-sectional view taken on line 5-5 of FIG. 4.

FIGS. 4 and 5 show apparatus 10 in a coupled configuration. In the coupled configuration, linkage 18, the outer surface of actuator 16, and the edge of second opening 23 of housing 14 are aligned, and the shape of the contact surfaces of collet fingers 22 are configured so that apparatus 10 remains in a coupled configuration after actuator 16 is pressed. Apparatus 10 returns to an uncoupled configuration when actuator 16 is pressed in the coupled configuration.

Figure 6:
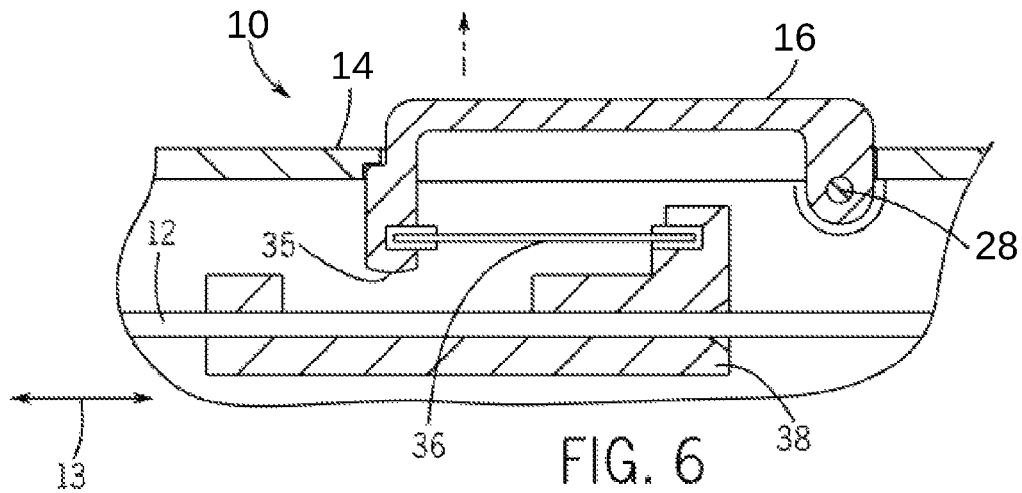
FIG. 6 is a detail longitudinal sectional view of one embodiment of the apparatus.
Figure 7:
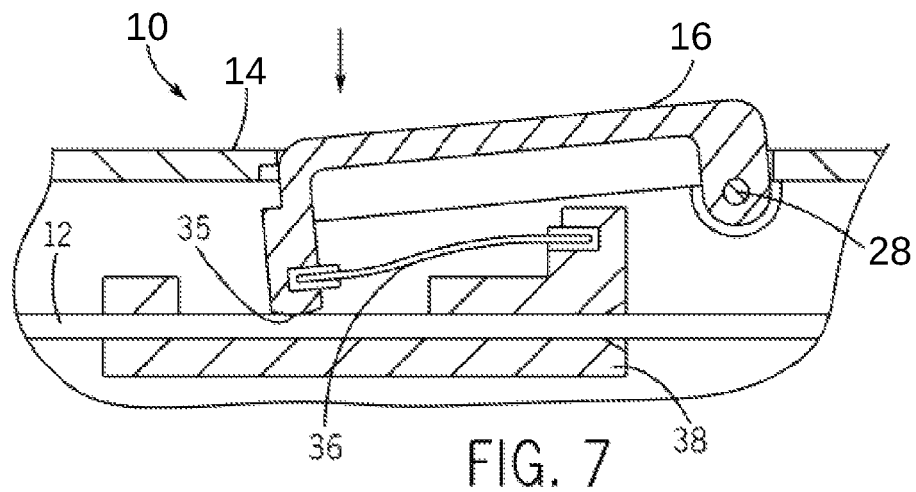
FIG. 7 is a detail longitudinal sectional view similar to FIG. 6 in a clamped configuration.

FIGS. 6 and 7 show is a detail longitudinal sectional view of one embodiment of the apparatus in an uncoupled and coupled configuration, respectively. In this embodiment, actuator 16 comprises a clamping portion 35, combined with wire guide 38, compress either side of guidewire 12 to couple it to apparatus 10. A leaf spring 36 is coupled to actuator 16 and wire guide 38. In this embodiment, leaf spring 36 comprises two layers that apply force in opposite directions. Therefore, leaf spring 36 applies outward force until it reaches an equilibrium point, and applies inward force beyond that point. Therefore, in the position shown in FIG. 6, leaf spring 36 applies an outward force, resisting compression of actuator 16. In the position shown in FIG. 7, leaf spring 36 applies an inward force that compresses clamping portion 35 against guidewire 12 and maintains apparatus 10 in a coupled configuration until actuator 16 is compressed again.

Figure 8:
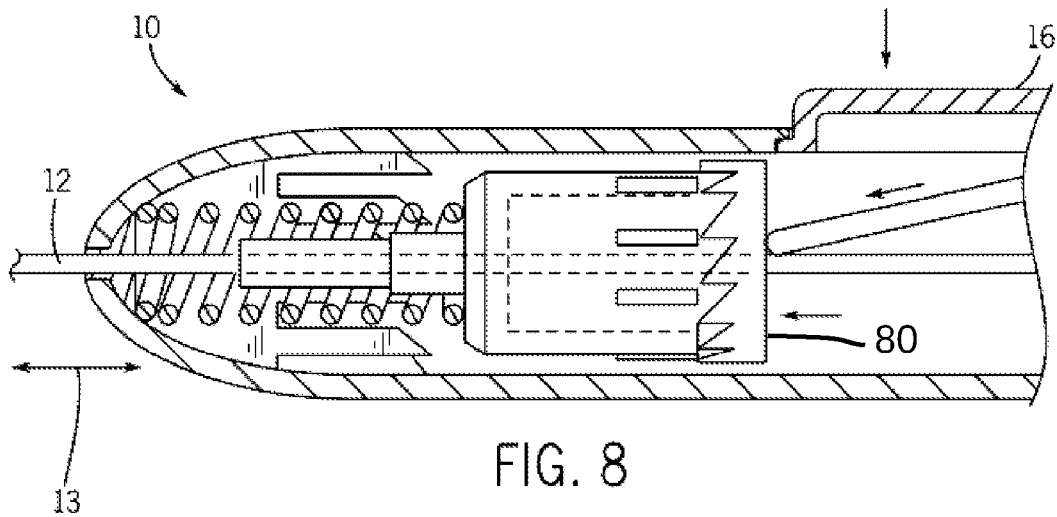
FIG. 8 is a detail longitudinal sectional view of one embodiment of the apparatus.

FIG. 8 is a detail longitudinal sectional view of one embodiment of the apparatus. In this embodiment, the clamping mechanism comprises ratchet 80. Ratchet 80 retains clamping mechanism in a coupled position once actuator 16 has been pressed. Ratchet 80 retains clamping mechanism in a coupled position until actuator 16 is pressed in the coupled position, at which point ratchet 80 toggles the clamping mechanism into an uncoupled position. In this embodiment, ratchet 80 rotates and moves axially relative to housing 14 to couple and uncouple apparatus 10 to wire 12. Ratchet 80 comprises teeth and flanges that engage teeth and grooves on housing 14.

In certain embodiments, the apparatus 10 described herein may include a hollow chamber of various materials such as plastic with a tapered tip. The surface of the housing 14 may be designed to have a minimal slip surface. The center of the device 10 may allow for various sizes of interventional wires 12 to pass freely through the device 10. Once the wire 12 has been passed through the device 10, securing the wire 12 in position may be the next step. The center chamber of the torque device 10 may include compressible material that surrounds the guidewire 12. Housing 14 of the device 10 may include one or multiple compression components at various angles that allow for single downward force to secure and hold wire 12 within the compressible central core. When the torque device 10 needs to be repositioned, actuator 16 can be released with a single handed motion without releasing or repositioning the hand.

As such, apparatus 10 is operated as follows. The user grasps apparatus 10 with one hand and the wire 12 with the other hand. The user advances the torque device 10 over the wire 12 by threading the wire 12 through first opening 21 of the torque device 10 to the desired position along the wire 12. Once the torque device 10 is at the selected position on the wire 12, use the tip of index finger 17 of the hand grasping apparatus 10 to compress the actuator 16. This will engage the compression mechanism to secure the torque device 10 at the desired position along the wire 12. At this point, the torque device 10 can be used while it is secured to the wire 12 to be able to assist in advancing the wire 12 and or rotating the wire 12 to desired positions. The same hand holding the torque device 10, that secured it to the wire 12, can now be used to advance, retract and rotate the secure wire 12 to any position without having to use a second hand, release the wire 12 or depend on visualization of the apparatus 10 for manipulation. When necessary to reposition or remove the torque device 10, actuator 16 is pressed again which disengages the device 10 from wire 12. This allows the user to freely reposition the torque device 10 along the wire 12 in a longitudinal or rotational position or remove it from the wire 12 completely without the use of a second hand or dependence of visual cues. This process may be repeated as many times as necessary to position the wire 12. At all times this device can be used with single hand manipulation which is a significant advancement over previous technology. The force used to engage or disengage this device 10 is perpendicular to the passed wire 12 and therefore a significant advancement over previous technology that often applies force parallel to the passed wire 12 which could lead to unexpected advancement or retraction of the passed wire 12.

Elements that could be added to improve the apparatus 10 described herein may include variations of the shape of the housing 14, variations of the number of actuators 16, variations of the color and the surface texture of the housing 10, variations of the shape of the proximal and distal end of the housing 14, variations of shape and size of the first opening 21 and second opening 23 of housing 14, variations of the actuator 16 in size, shape and texture, spring mechanisms 26, 36 may be of any shape that may allow the compression mechanism to engage and hold the wire 12 and then release when necessary by a second compression of actuator 16 and the housing 14 could be made to glow in the dark for higher visibility.

The present torque device 10 can be enlarged or minimized to any scale in order to accommodate any size wire 12 or structure needing to be advanced, retracted or rotated. Within any field of technology where a flexible structure would need to be positioned at its distal tip, this device may enable a more proximal fixed position that would allow for rotational and longitudinal movement of the distal end.

Although the invention has been described with reference to embodiments herein, those embodiments do not limit the invention. Modifications to those embodiments or other embodiments may fall within the scope of the invention.

What is claimed is:

1. An interventional guidewire assembly with improved guidewire control, comprising:
   a guidewire;
   a housing having a first opening that accommodates said guidewire and a second opening;
   an actuator that passes through the second opening that is actuated by a finger in a direction substantially perpendicular to an axis of said guidewire;
   a clamp operably coupled to said actuator that compresses said guidewire to couple said guidewire to said housing when said actuator is actuated;
   a retention spring that supplies pressure to compress said clamp against said guidewire; and
   a return spring that supplies pressure to remove said clamp from said guidewire.

2. The assembly of claim 1, wherein said return spring and said retention spring are two layers on a single leaf spring.

3. The assembly of claim 1, further comprising:
   a wire guide disposed in said housing in contact with said guidewire opposite said actuator;
   wherein said clamp comprises said wire guide and said actuator.

4. The assembly of claim 1, further comprising:
   a linkage that transfers motion from said actuator to said clamp and retains said clamp compressed against said guidewire after said actuator has been actuated.

5. An apparatus for precise control of a wire in two axes, comprising:
   a housing having a first opening that accommodates the wire and a second opening;
   an actuator that passes through the second opening that is actuated by a finger in a direction substantially perpendicular to an axis of the wire;
   a clamp operably coupled to said actuator that compresses the wire to couple the wire to said housing when pressure is applied to the actuator; and
   a pivot that couples said actuator to said housing and allows relative rotation between said actuator and said housing when pressure is applied to said actuator.

6. The apparatus of claim 5, further comprising:
   a return spring that supplies pressure to remove said clamp from said wire; and
   a retention spring that supplies pressure to compress said clamp against the wire.

7. The apparatus of claim 6, wherein said return spring and said retention spring are two layers on a single leaf spring.

8. The apparatus of claim 5, wherein said clamp is a collet.

9. The apparatus of claim 8, further comprising:
   a sleeve that compresses the collet against the wire when said actuator is actuated.

10. The apparatus of claim 5, further comprising:
    a wire guide disposed in said housing in contact with the wire opposite said actuator;
    wherein said clamp comprises said wire guide and said actuator.

11. The apparatus of claim 5, further comprising:
    a linkage that transfers motion from said actuator to said clamp and retains said clamp compressed against the wire after said actuator has been actuated.

* * * * *